(12) United States Patent
Wiltsey et al.

(10) Patent No.: US 11,793,909 B2
(45) Date of Patent: Oct. 24, 2023

(54) CROSSLINKABLE POLYMER COMPOSITIONS

(71) Applicant: Medtronic Vascular, Inc., Santa Rosa, CA (US)

(72) Inventors: Craig Wiltsey, Waltham, MA (US); Nikhita Mansukhani, Allston, MA (US); Jeffrey Groom, II, Belmont, MA (US); Kate Rielly, Belmont, MA (US); Changcheng You, Northbridge, MA (US); Danny Concagh, Medfield, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/699,457

(22) Filed: Mar. 21, 2022

(65) Prior Publication Data

US 2022/0265895 A1   Aug. 25, 2022

Related U.S. Application Data

(63) Continuation of application No. 17/111,878, filed on Dec. 4, 2020, now Pat. No. 11,311,648, which is a continuation of application No. 16/655,858, filed on Oct. 17, 2019, now abandoned, which is a continuation of application No. 16/288,163, filed on Feb. 28, 2019, now abandoned.

(60) Provisional application No. 62/809,254, filed on Feb. 22, 2019.

(51) Int. Cl.

| | |
|---|---|
| *A61L 27/18* | (2006.01) |
| *A61J 1/20* | (2006.01) |
| *A61L 27/02* | (2006.01) |
| *A61L 27/44* | (2006.01) |
| *A61L 27/50* | (2006.01) |
| *A61M 25/00* | (2006.01) |

(52) U.S. Cl.
CPC .............. *A61L 27/18* (2013.01); *A61J 1/20* (2013.01); *A61L 27/025* (2013.01); *A61L 27/446* (2013.01); *A61L 27/50* (2013.01); *A61L 2400/06* (2013.01); *A61L 2430/34* (2013.01); *A61L 2430/36* (2013.01); *A61M 25/00* (2013.01)

(58) Field of Classification Search
CPC ...... A61L 27/50; A61L 27/18; A61L 2430/36; A61L 2400/06; A61L 2430/34; C08L 83/04

See application file for complete search history.

(56) References Cited

U.S. PATENT DOCUMENTS

| | | |
|---|---|---|
| 3,674,690 A | 7/1972 | Clow et al. |
| 2007/0129672 A1 | 6/2007 | Jackson et al. |
| 2007/0162110 A1 | 7/2007 | Dave |
| 2012/0276008 A1* | 11/2012 | Walkenhorst ...... A61K 49/0457 424/9.1 |
| 2013/0078209 A1 | 3/2013 | Yu et al. |
| 2013/3017418 | 11/2013 | Freyman et al. |
| 2020/0268932 A1 | 8/2020 | Wiltsey et al. |

FOREIGN PATENT DOCUMENTS

| | | |
|---|---|---|
| WO | 2017/176709 A1 | 10/2017 |
| WO | 2018/081837 A1 | 5/2018 |
| WO | 2020/172665 A1 | 8/2020 |

OTHER PUBLICATIONS

Australian Examination Report No. 1 for Application No. 2020225561 filed Feb. 24, 2020, dated May 31, 2022, 4 pages.
International Search Report and Written Opinion dated Jun. 6, 2020 for PCT Application No. PCT/US2020/019496 filed Feb. 24, 2020, 11 pages.
AEROSIL R 8200 for Silicone Rubber, Technical Information 1209, Evonik Industries, Jul. 2015, 8 pages.

* cited by examiner

*Primary Examiner* — James W Rogers
(74) *Attorney, Agent, or Firm* — Brooks Kushman P.C.

(57) ABSTRACT

The present disclosure pertains to crosslinkable compositions and systems as well as methods for forming crosslinked compositions in situ, including the use of the same for controlling the movement of bodily fluid within a patient, among many other uses.

17 Claims, No Drawings

CROSSLINKABLE POLYMER COMPOSITIONS

CROSS REFERENCE TO RELATED APPLICATION

This application is a continuation of U.S. application Ser. No. 17/111,878, filed Dec. 4, 2020, now U.S. Pat. No. 11,311,648, which issued on Apr. 26, 2022, which is a continuation of U.S. application Ser. No. 16/655,858, filed Oct. 17, 2019 and entitled "CROSSLINKABLE POLYMER COMPOSITIONS", which is a continuation of U.S. application Ser. No. 16/288,163, filed Feb. 28, 2019 and entitled "CROSSLINKABLE POLYMER COMPOSITIONS", and which claims the benefit of U.S. Provisional Application No. 62/809,254, filed Feb. 22, 2019 and entitled "CROSSLINKABLE POLYMER COMPOSITIONS", each of which is hereby incorporated by reference.

FIELD OF THE DISCLOSURE

The present disclosure pertains to crosslinkable compositions and systems as well as methods for forming crosslinked compositions in situ, including the use of the same for controlling the movement of bodily fluid within a patient, among many other uses.

BACKGROUND

Crosslinkable compositions that are capable of forming crosslinked compositions in situ, have a number of important biomedical applications including vascular embolization, treatment of arteriovenous malformation, treatment of AV fistulas, treatment of abdominal aortic aneurysms, space filling and bulking (e.g. following surgical resection, or for cosmetic purposes), prevention of tissue adhesion, hernia repair, prevention or treatment of reflux, temporary or permanent occlusion of body lumens for a variety of applications including sterilization and prevention of calculus migration during lithotripsy, treatment of hemorrhage, particularly from non-compressible or difficult-to-visualize wounds, and other applications.

The diversity of applications for in-situ-forming crosslinked compositions reflects significant advantages possessed by such implants including, without limitation the ability to deliver in-situ-forming crosslinked compositions to closed cavities, for example intravascularly, the ability to deliver in-situ-forming crosslinked compositions to difficult-to-access body sites, the ability of in-situ-forming crosslinked compositions to fill empty space, potential space, or fill space filled with blood, support surrounding tissues, and so forth.

SUMMARY OF THE INVENTION

The present disclosure pertains to crosslinkable compositions and systems as well as methods for forming crosslinked compositions in situ.

In some aspects, the present disclosure pertains to a composition comprising a first polysiloxane having two or more unsaturated groups (i.e., groups containing carbon-carbon double bonds and/or groups containing carbon-carbon triple bonds), a first silanol compound, a first filler, a first hydride material having two or more hydride groups, and a catalyst for catalyzing a reaction between the unsaturated groups and the hydride groups, in which (a) the composition may have a viscosity as measured by oscillatory rheology at 0.1 Hz and 1% strain at 25° C. that is at least ten-fold, beneficially at least one-hundred-fold, more beneficially at least five-hundred-fold, greater than a viscosity of the composition as measured by flow rheology at a frequency of 30 Hz at 25° C., (b) the composition may cure when measured at 37° C., within a time period of 1 minute to 120 minutes, beneficially 15 minutes to 120 minutes, (c) after being allowed to anneal for a period of 7 days at 70° C., the composition may have a viscosity as measured using oscillatory rheology at a frequency of 0.1 Hz and a strain of 1% at 25° C. or 37° C. is in the range of 3,000 to 40,000 Pa*s, (d) the composition may have a combination of properties (a) and (b), (e) the composition may have a combination of properties (a) and (c), (f) the composition may have a combination of properties (b) and (c), or (g) the composition may have a combination of properties (a), (b) and (c).

In some embodiments, which may be used in conjunction with the preceding aspects, the composition may further comprise a first physical crosslinking agent comprising a plurality of hydrogen bonding groups.

In some embodiments, which may be used in conjunction with any of the above aspects and embodiments, the composition may further comprise an imaging agent, such as a radiopaque agent, an MRI contrast agent or an ultrasound contrast agent.

In some embodiments, which may be used in conjunction with any of the above aspects and embodiments, the unsaturated groups may be selected from $-CH=CH_2$ and $-C\equiv CH$ groups.

In some embodiments, which may be used in conjunction with any of the above aspects and embodiments, the first polysiloxane having two or more unsaturated groups may be a vinyl-terminated polysiloxane, an acrylate-terminated polysiloxane, a methacrylate-terminated polysiloxane, or an alkyne-terminated polysiloxane.

In some embodiments, which may be used in conjunction with any of the above aspects and embodiments, the first hydride material may have between 2 and 20 hydride groups.

In some embodiments, which may be used in conjunction with any of the above aspects and embodiments, the catalyst may be selected from a platinum catalyst, a rhodium catalyst, a ruthenium catalyst, a palladium catalyst, an iridium catalyst, a boron trihydride catalyst, and a phosphine catalyst.

In some embodiments, which may be used in conjunction with any of the above aspects and embodiments, the first silanol compound may be a hydroxy-terminated polysiloxane.

In some embodiments, which may be used in conjunction with any of the above aspects and embodiments, the first filler may be a silica filler characterized by a surface area of 100-500 m²/g.

In some aspects, the present disclosure pertains to a system, which comprises two or more composition portions that when combined form an composition in accordance with any of the above aspects and embodiments, and the two or more composition portions may include a first composition portion and a second composition portion.

In some aspects, the present disclosure pertains to a system, which comprises (a) an composition in accordance with any of the above aspects and embodiments and (b) a delivery device containing the composition. The system may be used, for example, for controlling the movement of bodily fluid within a patient. In some of these embodiments, the system may comprise two or more composition portions that when combined form the composition, and the two or more composition portions may include a first composition portion and a second composition portion separated from each other within the delivery device.

In some embodiments, which may be used in conjunction with any of the above aspects and embodiments, the first composition portion may comprise the first polysiloxane having two or more unsaturated groups, the first silanol compound, and the first filler, the second composition portion may comprise the first hydride material having two or more hydride groups, a second silanol compound, and a second filler; the catalyst may be within at least one of the first and second composition portions; the first and second silanol compounds may be the same or different; and the first and second fillers may be the same or different.

In some embodiments, which may be used in conjunction with any of the above aspects and embodiments, the first and second composition portions may each have a viscosity as measured by oscillatory rheology at 0.1 Hz and 1% strain at 25° C. that is at least ten-fold, beneficially at least one-hundred-fold, more beneficially at least five-hundred-fold, greater than a viscosity of the composition as measured by flow rheology at a frequency of 30 Hz at 25° C. In certain of these embodiments, the (a) the first composition portion may further comprise a first physical crosslinking agent comprising a plurality of hydrogen bonding groups and the second composition portion may further comprise a second physical crosslinking agent comprising a plurality of hydrogen bonding groups, wherein the first and second physical crosslinking agents may be the same or different and/or (b) the first composition portion may further comprise a first imaging agent and the second composition portion may further comprise a second imaging agent, wherein the first and second imaging agents may be the same or different.

In some embodiments, which may be used in conjunction with any of the above aspects and embodiments, the delivery device may be configured to mix the first and second composition portions to form the composition in the delivery device and to deliver the composition into a body of the patient. In certain of these embodiments, the delivery device may comprise a first container comprising the first composition portion, a second container comprising the second composition portion, a mixer configured to mix the first and second composition portions, and a catheter.

In certain aspects, the present disclosure pertains to a composition comprising a polysiloxane having two or more alkoxy groups, a silanol compound having two or more silanol groups, and a first filler, in which (a) the composition may have a viscosity as measured by oscillatory rheology at 0.1 Hz and 1% strain at 25° C. that is at least ten-fold, beneficially at least one-hundred-fold, more beneficially at least five-hundred-fold, greater than a viscosity of the composition as measured by flow rheology at a frequency of 30 Hz at 25° C., (b) the composition may cure, when measured at 37° C., within a time period of 1 minute to 120 minutes, beneficially 15 minutes to 120 minutes, (c) after being allowed to anneal for a period of 7 days at 70° C., the composition may have a viscosity as measured using oscillatory rheology at a frequency of 0.1 Hz, and a strain of 1% at 25° C. or 37° C. may be in the range of 3,000 to 40,000 Pa*s, (d) the composition may have a combination of properties (a) and (b), (e) the composition may have a combination of properties (a) and (c), (f) the composition may have a combination of properties (b) and (c), or (g) the composition may have a combination of properties (a), (b) and (c).

In some embodiments, which may be used in conjunction with the preceding aspects, the polysiloxane may be a poly(alkoxysiloxane).

In some embodiments, which may be used in conjunction with any of the above aspects and embodiments, the alkoxy groups of the polysiloxane may be selected from ethoxy groups.

In some embodiments, which may be used in conjunction with any of the above aspects and embodiments, the silanol compound may be a hydroxy-terminated polysiloxane.

In some embodiments, which may be used in conjunction with any of the above aspects and embodiments, the first filler may be a silica filler characterized by a surface area of 100-500 $m^2/g$.

In some embodiments, which may be used in conjunction with any of the above aspects and embodiments, the composition may further comprise a catalyst for catalyzing a reaction between the alkoxy groups and the silanol groups. In some of these embodiments, the catalyst may be selected from a tin-based catalyst and a titanium-based catalyst.

In some embodiments, which may be used in conjunction with any of the above aspects and embodiments, the composition further may comprise a diluent. In some of these embodiments, the diluent may be trialkylsiloxy-terminated polysiloxane.

In some embodiments, which may be used in conjunction with any of the above aspects and embodiments, the composition may further comprise an imaging agent.

In some embodiments, which may be used in conjunction with any of the above aspects and embodiments, the composition may further comprise a physical crosslinking agent comprising a plurality of hydrogen bonding groups.

In some aspects, the present disclosure pertains to a system, which comprises two or more composition portions that when combined form a composition in accordance with any of the above aspects and embodiments, and the two or more composition portions may include a first composition portion and a second composition portion.

In some aspects, the present disclosure pertains to a system, which comprises (a) a composition in accordance with any of the above aspects and embodiments and (b) a delivery device containing the composition. The system may be used, for example, for controlling the movement of bodily fluid within a patient. In some of these embodiments, the system may comprise two or more composition portions that when combined form the composition, and the two or more composition portions may include a first composition portion and a second composition portion separated from each other within the delivery device.

In some embodiments, which may be used in conjunction with any of the above aspects and embodiments, the first composition portion may comprise the polysiloxane having two or more alkoxy groups, the silanol compound having two or more silanol groups, and the first filler; and the second composition portion may comprise a second filler, the catalyst for catalyzing a reaction between the alkoxy groups and the silanol groups, and a diluent. In some of these embodiments, (a) the first composition portion may further comprise a first imaging agent and the second composition portion may further comprise a second imaging agent, wherein the first and second imaging agents may be the same or different and/or (b) the first composition portion may further comprise a first physical crosslinking agent comprising a plurality of hydrogen bonding groups and the second composition portion may further comprise a second physical crosslinking agent comprising a plurality of hydrogen bonding groups, wherein the first and second physical crosslinking agents may be the same or different.

In some embodiments, which may be used in conjunction with any of the above aspects and embodiments, the first and second composition portions may each have a viscosity as measured by oscillatory rheology at 0.1 Hz and 1% strain at 25° C. that is at least ten-fold, beneficially at least one-hundred-fold, more beneficially at least five-hundred-fold, greater than a viscosity of the composition as measured by flow rheology at a frequency of 30 Hz at 25° C.

In some embodiments, which may be used in conjunction with any of the above aspects and embodiments, the delivery device may be configured to mix the first and second composition portions to form the composition in the delivery device and to deliver the composition into a body of the patient.

In some embodiments, which may be used in conjunction with any of the above aspects and embodiments, the delivery device may comprise a first container comprising the first composition portion, a second container comprising the second composition portion, a mixer configured to mix the first and second composition portions, and a catheter.

DETAILED DESCRIPTION

As used herein, a material is described as a "fluid" if it is flowable, as is the case with, for example, liquid, semi-solid, and viscoelastic materials.

For the purposes of this disclosure, the terms "crosslinkable composition," "crosslinkable addition-cure composition," "crosslinkable condensation-cure composition," "curable composition," "curable addition-cure composition," and "curable condensation-cure composition," generally refer to a polymer-based fluid that is capable of being delivered to a delivery site, after which crosslinking (i.e., curing) of the material continues to progress at the delivery site. For the purposes of this disclosure, the term "addition-cure" refers to a process in which components are cross-linked (i.e., cured) and in which there are no byproducts of the crosslinking process. An example of an addition-cure process is one in which the reactants include one or more components comprising carbon-carbon multiple bonds or carbon-other-atom multiple bonds (e.g., alkene, alkyne, carbonyl, imine, etc.) are reacted and in which there are no byproducts of the reaction. One specific example of an addition-cure process employed hereinbelow is the reaction a vinyl group with a hydride to produce an ethylene bridge. For the purposes of this disclosure, the term "condensation-cure" refers to a process in which components are cross-linked (i.e., cured) and in which water, alcohol or acid is a byproduct of the crosslinking process. An example of a condensation-cure process is one in which one or more components comprising silanol groups are reacted one or more components comprising alkoxy groups and in which alcohol is a byproduct of the reaction as described hereinbelow.

Although the detailed description of the present disclosure sets forth addition-cure compositions, systems and methods as well as composition-cure compositions, systems and methods, it should be understood that various aspects of the present disclosure are not so limited.

In various aspects, compositions in accordance with the present disclosure are delivered into a body of a patient as discussed in more detail below. For example, the compositions may be dispensed onto any tissue or into any body cavity or body lumen of a patient, including, for example, a fallopian tube, a ureter, or the vasculature of a patient). For example, the compositions may be used in a number of applications including vascular embolization, treatment of arteriovenous malformation, treatment of AV fistulas, treatment of abdominal aortic aneurysms, intracranial aneurysms or pulmonary aneurysm, space filling and bulking in a variety of tissues, prevention of tissue adhesion, hernia repair, treatment of reflux, temporary or permanent occlusion of body lumens for a variety of applications including sterilization and prevention of calculus migration during lithotripsy, and treatment of hemorrhage.

In various aspects, the compositions described herein are injected or deposited into a delivery site in a body of a patient through the use of a delivery system. In various embodiments, the delivery system may comprise a catheter. As used herein, a "catheter" is any device that may be introduced into or adjacent to a patient's body or target location within a patient's body, and comprises at least one lumen of any appropriate size, shape or configuration for the movement of fluid therethrough. As used herein, compositions described as being "injected", "deposited", "delivered" and the like include compositions that are placed via a delivery system at a delivery location on or within a patient's body using any suitable means, including syringe-based injection. Depending on fluid viscosity, a hand-powered syringe-assist, pneumatic or mechanical pressure pump, or other device may be used to control the flow rate and/or improve ease/force of injection.

The compositions of the present disclosure typically include one or more polysiloxane-based polymers (i.e., polymers having repeating —Si—O— bonds in the polymer backbone). Polysiloxane-based polymers for use in the present disclosure include those comprising homopolymer and/or copolymer regions consisting of, or containing, one or more organo-siloxane monomers, including dialkylsiloxane monomers, diarylsiloxane monomers and/or alkylarylsiloxane monomers, such as dimethylsiloxane, diethylsiloxane, methylethylsiloxane, methylphenylsiloxane and/or diphenylsiloxane monomers, to name a few examples. In various beneficial embodiments described herein, polydialkylsiloxane-based polymers, including polydimethylsiloxane (PDMS)-based polymers, are employed. PDMS-based polymers are beneficial for use in the present disclosure for a variety of reasons, including low relative viscosity at higher molecular weights (MW), their well-established use in medical devices, and their inherent biocompatibility. While polysiloxane-based polymers are exemplified, it is to be understood that other biostable, elastomeric polymers may be employed in place of or in addition to the polysiloxane-based polymers described herein, including natural rubbers, synthetic rubbers such as polydienes, polyolefins such as polyisobutylene, polyurethanes, polyureas, polyalkylene oxides such as polyethylene oxide (PEO) and polypropylene oxide (PPO), as well as copolymers, including block copolymers, of two or more of the foregoing.

As used herein, a "silanol" or "silanol compound" is a compound that comprises one or more silanol (Si—OH) groups and is commonly a polysiloxane-based polymer that comprises two or more silanol groups, for example a hydroxy-terminated PDMS, among other examples.

In some aspects, compositions in accordance with the present disclosure (also referred to herein as "addition-cure compositions") comprise a hydride material having two or more hydride groups and a polysiloxane having two or more unsaturated groups. In various embodiments, the addition-cure compositions may further comprise a silanol compound, a filler, a catalyst for catalyzing a reaction between the hydride groups of the hydride material and the unsaturated groups of the polysiloxane, or a combination of any two or all three of the foregoing additional components. In certain embodiments, the addition-cure compositions may comprise further additional components, including, for example, a first physical crosslinking agent comprising a plurality of hydrogen bonding groups, an imaging agent, or both.

In certain embodiments, (a) the addition-cure compositions have a viscosity as measured by oscillatory rheology at 0.1 Hz and 1% strain at 25° C. that is at least ten-fold, beneficially at least one-hundred-fold, more beneficially at least five-hundred-fold, greater than a viscosity of the composition as measured by flow rheology at a frequency of 30 Hz at 25° C., (b) the addition-cure compositions cure when measured at 37° C. within a time period of 1 minute to 120 minutes, beneficially 15 minutes to 120 minutes, (c) after being allowed to anneal for a period of 7 days at 70° C., the addition-cure compositions have a viscosity as measured using oscillatory rheology at a frequency of 0.1 Hz and a strain of 1% at 25° C. or 37° C. is in the range of 3,000 to 40,000 Pa*s, (d) the addition-cure compositions have a combination of properties (a) and (b), (e) the addition-cure compositions have a combination of properties (a) and (c), (f) the addition-cure compositions have a combination of properties (b) and (c), or (g) the addition-cure compositions have a combination of properties (a), (b) and (c).

Rheological measurements are made using a TA Instruments (Newcastle, DE, USA) Discovery HR-1 rheometer. For property (a), the composition is placed into a 25 mm parallel plate setup (using sandblasted plates to avoid slip), a Peltier system (TA Instruments) is used to control that temperature and maintain a gap of 1000 microns, and (i) a first viscosity is measured using oscillatory rheology at 1% strain and 0.1 Hz (lower shear) at 25° C., (ii) a second viscosity is measured using flow rheology at a frequency of 30 Hz at 25° C. (higher shear), and a determination is made as to whether the first viscosity value is at least ten-fold, beneficially at least one-hundred-fold, more beneficially at least five-hundred-fold greater than the second viscosity value. For property (b), the composition is loaded onto a rheometer with a 25 mm parallel plate setup (see above) and measurements are taken at constant frequency and strain (f=10 rad/s, γ=1%) over the course of 90 minutes to observe the cure time and profile; gel time (time of cure) is defined as the time at which a peak of the phase angle (δ) is observed. For property (c), the composition is allowed to anneal for a period of 7 days at 70° C., after which viscosity is measured using oscillatory rheology employing the TA Instruments system described above at a temperature of 25° C. or 37° C., a frequency of 0.1 Hz and a strain of 1%. Viscosity measured by flow rheology provides an indication of the properties of the composition under shear conditions similar to the conditions placed on the composition during delivery from a delivery device. Viscosity measured by flow rheology provides an indication of the properties of the composition within the body (e.g., in an aneurysm) where shear conditions are experienced having low strain and low frequency. Curing time will change based on temperature and curing will take place in the within the body at 37° C.; a time period of 15 minutes being selected in certain embodiment to correspond approximately to the time required to fill a space (e.g., an aneurysm) within the body, and 120 minutes being selected in certain embodiments to allow the material to cure within a time selected to correspond approximately the of a procedure.

In various aspects, addition-cure compositions in accordance with the present disclosure may be delivered into a body of a patient as discussed in more detail below.

In certain embodiments, the addition-cure compositions may contain 500-5000 grams of the polysiloxane having two or more unsaturated groups per mole of the hydride groups. For the purposes of this disclosure, "unsaturated groups" are groups with less than the maximum number of hydrogen atoms per carbon (not saturated with hydrogen atoms), including groups with carbon-carbon double or triple bonds such as alkene or alkyne groups. Specific examples of polysiloxanes having two or more unsaturated groups include unsaturated-group-terminated polysiloxanes such as vinyl-terminated PDMS, acrylate-terminated PDMS, or methacrylate-terminated PDMS).

It is further noted that an excess amount of hydride groups (stoichiometrically) relative to vinyl groups can lead to the production of gas. Thus, in those embodiments, where gas is not desired, the addition-cure composition may have a ≥0.9:1 vinyl-group-to-hydride-group molar ratio.

In certain embodiments, the weight average molecular weight of all of the substituents in the addition-cure compositions, other than the filler and the imaging agent (if present), ranges from 2,000 to 25,000 Da, typically 4,000 to 16,000 Da.

In some embodiments, addition-cure compositions of the present disclosure may be provided by combining a first addition-cure composition portion that comprises a polysiloxane having two or more unsaturated groups (which may beneficially have a viscosity as measured by oscillatory rheology as described above that is at least ten-fold, beneficially at least one-hundred-fold, more beneficially at least five-hundred-fold, greater than a viscosity as measured by flow rheology relative as described above) with a second addition-cure composition portion that comprises a hydride material having two or more hydride groups (which may beneficially have a viscosity as measured by oscillatory rheology as described above that is at least ten-fold, beneficially at least one-hundred-fold, more beneficially at least five-hundred-fold, greater than a viscosity as measured by flow rheology as described above) to form a crosslinkable addition-cure composition (e.g., one suitable for immediate delivery to a subject and preferably having one or more viscosity and/or cure characteristics such as those described above). A catalyst for catalyzing a reaction between the unsaturated groups of the polysiloxane and the hydride groups of the hydride material may be provided within either one or both of the first and second addition-cure composition portions. Typically, the catalyst is included in the first addition-cure composition portion containing the polysiloxane having two or more unsaturated groups but not with the second addition-cure composition portion containing the hydride material having two or more hydride groups. Typically, the ratio of the volume of the first addition-cure composition portion to the volume of the second addition-cure composition portion is approximately equal (~1:1), typically ranging, for example, from 2:1 to 1:2, more typically 1.5:1 to 1:1.5, among other possible proportions. To enhance mixing, the viscosities of the first and second addition-cure composition portions will be similar, for example, the oscillatory viscosity of the first and second addition-cure composition portions at a frequency of 0.1 Hz at 25° C. may be within +/−60% of one another.

In some embodiments, the crosslinkable addition-cure compositions may be provided by combining (a) a first addition-cure composition portion that comprises a first polysiloxane having two or more unsaturated groups, a first silanol compound, and a first filler with (b) a second addition-cure composition portion that comprises a hydride material having two or more hydride groups, a second silanol compound (which may be the same as or different from the first silanol compound), and a second filler (which may be the same as or different from the first filler). In various embodiments, a catalyst for catalyzing a reaction between the unsaturated groups of the polysiloxane and the hydride groups of the hydride material is provided within either one or both of the first and second addition-cure composition portions.

In various embodiments, a physical crosslinking agent comprising a plurality of hydrogen bonding groups (e.g., —OH groups, —NH groups, etc.) may be provided within either one or both of the first and second addition-cure composition portions. In embodiments where a first physical crosslinking agent is provided within the first addition-cure composition portion and a second physical crosslinking agent is provided within the second addition-cure composition portion, the first and second physical crosslinking agents may be the same or different.

In various embodiments, an imaging agent may be provided within either one or both of the first and second addition-cure composition portions. In embodiments where a first imaging agent is provided within the first addition-cure composition portion and a second imaging agent is provided within the second addition-cure composition portion, the first and second imaging agents may be the same or different.

In some embodiments, the unsaturated groups of the polysiloxane having two or more unsaturated groups may be selected from —CH═CH$_2$ and —C≡CH groups. In some embodiments, the polysiloxane having two or more unsaturated groups has a weight average molecular weight that ranges from 4,000 to 20,000 Da.

In some embodiments, the polysiloxane having two or more unsaturated groups is a vinyl-terminated polysiloxane, an acrylate-terminated polysiloxane, a methacrylate-terminated polysiloxane, or an alkyne-terminated polysiloxane.

Vinyl-terminated PDMS, e.g.,

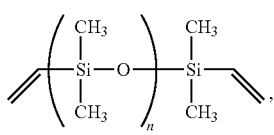

where n is an integer, is available, for instance, as DMS-V22 from Gelest, Inc., Morrisville, PA, USA or GP-977 from Genesee Polymers Corporation, Burton, MI, USA.

For purposes of the present disclosure a "hydride group" is a reactive group in which hydrogen is bonded to another atom. Examples of hydride material having two or more hydride groups include both small molecule hydrides and polymeric hydrides including multifunctional PDMS hydride, for example,

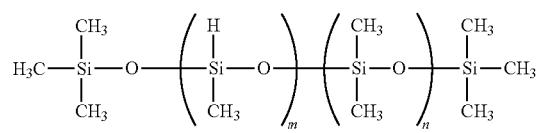

where n and m are integers, such as HMS-082 or HMS-151 from Gelest, Inc. and GP-236 from Genesee Polymers Corporation. In certain embodiments, hydride materials are employed which contain from 2 to 20 hydride groups per molecule, typically from 3 to 10 hydride groups per molecule, more typically from 5-6 hydride groups per molecule. While silicon hydride (Si—H) groups are exemplified throughout the present disclosure, it is to be understood that other hydride groups, in particular, carbon hydride (C—H) groups, may be used in place of the various silicon hydride groups that are described herein. For example, a hydride material comprising two or more methyl groups may react with a polysiloxane having two or more unsaturated groups via a peroxide initiator in some embodiments.

The use of such hydride materials can result in relatively fast reaction kinetics (e.g. with cure occurring in less than 5 minutes). To the extent that it may be desirable to retard the reaction rate to some extent (for example, in the case of AAA treatment, a cure time of 15-120 minutes may be desirable), crosslinking reaction kinetics may be slowed by the addition of a polyvinylated small molecule catalyst modifier such as 1,3,5,7-tetravinyl-1,3,5,7-tetramethylcyclotetrasiloxane,

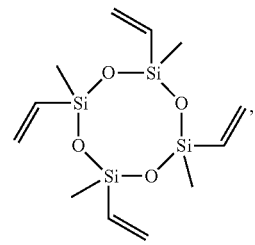 [SMILES: C=C[Si]1(C)O[Si](C)(C=C)O[Si](C)(C=C)O[Si](C)(C=C)O1]

available from Gelest, among others.

Examples of hydride material having two or more hydride groups further include hydride-terminated PDMS, for example,

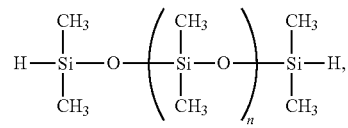

where n is an integer, such as DMS-H11 and DMS-H21 available from Gelest, Inc. or GP-536 and GP-499 available from Genesee Polymers Corporation. In certain embodiments, a mixture of hydride-terminated PDMS may be employed, for example, a mixture of hydride material with a weight average molecular weight of 4-10 kDa and a hydride material with a weight average molecular weight of 11-20 kDa may be employed.

In various embodiments, the catalyst for catalyzing a reaction between unsaturated groups and hydride groups in the addition-cure compositions of the present disclosure may be selected from a platinum catalyst, a rhodium catalyst, a ruthenium catalyst, a palladium catalyst, an iridium catalyst, a boron trihydride catalyst, and a phosphine catalyst.

In various embodiments, silanol compounds for use in the addition-cure compositions of the present disclosure include silanol-terminated polymers, such as hydroxy-terminated polysiloxanes, for example,

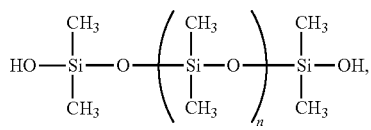

where n is an integer. Specific examples of such materials include DMS-S12, DMS-S21 and DMS-S31 available from Gelest, Inc. In certain embodiments, hydroxy-terminated polysiloxanes may be selected which have a weight average molecular weight that is less than 4,000 Daltons.

For purposes of this disclosure, a "filler" is a solid component added to a composition to impart rheological modification, mechanical property modification, or both. Fillers for use in the present disclosure include various inorganic fillers, such as carbon fillers (e.g., carbon black), metal oxide fillers (e.g., titanium dioxide, zinc oxide, etc.), carbonate fillers (e.g., calcium carbonate), and silica fillers. Silica fillers, including fumed, precipitated, platelet and passivated silica fillers, are available in a range of sizes and surface areas and are available from a variety of vendors, including Sigma Aldrich. In certain embodiments, silica fillers may be characterized by a surface area of 100-500 m$^2$/g, among other possible values. As a general rule of thumb, increased viscosity may be achieved by using fillers with higher surface area, fillers with smaller particle size (which is related to surface area), or both. Fillers for use in the present disclosure may range in aggregate particle size from 0.1 to 1.0 μm, among other values, for example, ranging from 0.01 to 10.0 μm in aggregate particle size, among other possibilities.

Typically, the addition of the fillers will improve mechanical properties (e.g., tensile strength, compressive strength, elastic modulus and/or durometer) of the final cured material. In certain embodiments, the fillers are selected to provide the addition-cure compositions of the present disclosure (i.e., the crosslinkable addition-cure compositions, as well as the first and second addition-cure composition portions used to form the same) with shear-thinning or thixotropic fluid properties, for example, to ensure that the compositions have a viscosity, as measured by oscillatory rheology at 0.1 Hz and 1% strain at 25° C. that is preferably by at least ten-fold, beneficially at least one-hundred-fold, more beneficially at least five-hundred-fold, greater than a viscosity as measured by flow rheology at a frequency of 30 Hz at 25° C. This property is particularly beneficial for delivery through low profile delivery systems, as the application of pressure (shear) in the delivery system lowers the apparent viscosity of the fluids, allowing the fluids to be more readily injected. Upon the removal of shear (e.g., as the fluid exits the delivery system) the composition returns to a more structured form, with high apparent viscosity helping to prevent migration of the injected material (e.g. in the case of injection into an aneurysm sac, preventing non-target embolization while being able to fill the entire aneurysm sac and to flow around any prosthesis, such as a stent graft, in the sac).

Other ways to adjust the rheological characteristics of the compositions of the present disclosure include adjusting either the surface area of the filler or particle size of the filler, with higher surface area and smaller particles generally expected to increase the interactions between the filler and the surrounding medium, therefore providing higher viscosity).

It has been found that, in certain embodiments, the inclusion of a silanol compound can enhance the shelf stability of the first and second addition-cure composition portions described herein. For example, it has been found that the addition of a silanol compound can counteract a decrease in viscosity over time of a mixture of vinyl-terminated PDMS, hydride PDMS and silica that might otherwise occur in the absence of the silanol compound. In certain embodiments, a weight ratio of silanol compound to silica of between 2:1 and 1:2, preferably 1:1, may be useful. In some embodiments, silanol compounds having a weight average molecular weight (MW) ranging, for example, from 100 to 2000, typically from 200 to 1000, more typically from about 500 to 600 may be employed.

In some embodiments, imaging agents for use in the addition-cure compositions of the present disclosure may be selected, for example, from MRI (magnetic resonance imaging) contrast agents, ultrasound contrast agents, and radiopaque agents, including for instance, radiopaque metals, radiopaque metal alloys, radiopaque metal oxides and radiopaque polymers, including iodinated polymers. In particular embodiments, the radiopaque agent may be selected from tantalum, tungsten, bismuth (III) oxide, zinc oxide, titanium dioxide and zinc titanate. Contrast agents for use in conjunction with magnetic resonance imaging (MRI), include contrast agents that contain elements with relatively large magnetic moment such as gadolinium, manganese and iron (e.g., Gd(III), Mn(II), Fe(III), etc.) and compounds (including chelates) containing the same, such as gadolinium ion chelated with diethylenetriaminepentaacetic acid. Contrast agents for use in conjunction with ultrasound imaging include microbubbles filled with suitable gases such as air, carbon dioxide, oxygen, nitrogen, sulfur hexafluoride, perfluorobutane or octafluoropropane, among others.

In various embodiments, physical crosslinking agents for use in the addition-cure compositions of the present disclosure may comprise a plurality of hydroxy (—OH) groups as hydrogen bonding groups. Examples of physical crosslinking agents include, hydroxy-terminated polymers and dendrimers such as hydroxy-terminated polysiloxanes (e.g., carbinol (hydroxy) terminated polydimethylsiloxane), hydroxy-terminated poly(alkylene oxides) including hydroxy-terminated polyethylene oxide and hydroxy-terminated polypropylene oxide, and hydroxy-terminated polyvinyl alcohol. Such hydroxy-terminated polymers may be, for example, linear, or may be multiarmed or dendritic, for example, having three, four, five, six or more arms, one specific example of which is a three-arm polymer of the formula,

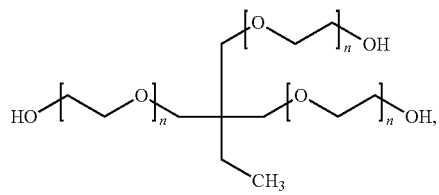

where n is an integer. Other examples include sugars, such as sucrose, cellulose, glucose, and dextrose, and potassium phthalate, polyols (e.g., glycerol, diglycerol, triglycerol, tetraglycerol, pentaglycerol, hexaglycerol, ethylene glycol, propylene glycol, butylene glycol, 1,5-pentane diol, 1,6-hexane diol, trimethylolpropane, 1,2,6-hexane triol, pentaerythritol, sorbitol, mannitol, hydroxypropylmethylcellulose or hydroxypropylethylcellulose) and acrylates (e.g. poly (acrylic acid), 2-hydroxyethylmethacrylate, poly (methyl methacrylate-co-ethyl acrylate)). Such physical crosslinkers may be provided, for example, in a concentration ranging from 0.5 to 5 wt %, typically 1.0 to 4.0 wt %, more typically about 1.25-3.5 wt %, among other possible amounts.

In certain embodiments, the physical crosslinking agents may be selected to increase the resting viscosity (i.e., the zero-shear viscosity) of the addition-cure compositions of the present disclosure (i.e., the crosslinkable addition-cure compositions, as well as the first and second addition-cure composition portions used to form the same), without significantly impacting the shear-thinning characteristics of the material.

In this regard, as noted above, the addition of a silanol compound can be useful in providing enhanced stability in some embodiments. The addition of a silanol compound, however, can act to decrease the resting viscosity of the addition-cure compositions described herein. While viscosity may be increased by providing additional filler, this can make delivery more difficult. However, by providing physical crosslinking agents such as those described hereinabove, resting viscosity can be increased, without significantly impacting the shear-thinning characteristics of the material. Without being bound by theory, it is hypothesized that such molecules can provide additional hydrogen bonding by bridging between silica particles and/or PDMS chains.

In certain embodiments, it has been found that the average molecular weight of the first and second addition-cure composition portions can be adjusted to enhance the cohesiveness (the ability of the first and second addition-cure composition portions to remain attached to a larger bulk rather than breaking into small pieces) under shear. In these embodiments, the overall molecular weight of the first and second addition-cure composition portions (i.e., the weight average molecular weight of all of the substituents in the addition-cure compositions, other than filler and imaging agent, if present) may be less than 12,000 Da, for example ranging from 4,000 to 10,000 Da.

In various additional aspects, compositions in accordance with the present disclosure (also referred to herein as "condensation-cure compositions") may comprise a polysiloxane having two or more alkoxy groups, a silanol compound having two or more silanol groups, and an optional filler. In certain embodiments, the condensation-cure compositions may further comprise additional components, including, for example, a catalyst for catalyzing a reaction between the alkoxy groups and the silanol groups, a diluent, a physical crosslinking agent comprising a plurality of hydrogen bonding groups, an imaging agent, or a combination of any two, any three or all four of the foregoing additional components.

In certain embodiments, (a) the condensation-cure compositions of the present disclosure may have a viscosity as measured by oscillatory rheology at 0.1 Hz and 1% strain at 25° C. that is at least ten-fold, beneficially at least one-hundred-fold, more beneficially at least five-hundred-fold, greater than a viscosity as measured by flow rheology at a frequency of 30 Hz at 25° C., (b) the condensation-cure compositions may cure when measured at 37° C. within a time period of 1 minute to 120 minutes, beneficially 15 minutes to 120 minutes, (c) after being allowed to anneal for a period of 7 days at 70° C., the condensation-cure compositions may have a viscosity as measured using oscillatory rheology at a frequency of 0.1 Hz and a strain of 1% at 25° C. or 37° C., is in the range of 3,000 to 40,000 Pa*s, (d) the condensation-cure compositions have a combination of properties (a) and (b), (e) the condensation-cure compositions have a combination of properties (a) and (c), (f) the condensation-cure compositions have a combination of properties (b) and (c), or (g) the condensation-cure compositions have a combination of properties (a), (b) and (c).

In some embodiments, condensation-cure compositions in accordance with the present disclosure may be delivered into a body of a patient as discussed in more detail below.

In various embodiments, compositions in accordance with the present disclosure may be provided by combining a first condensation-cure composition portion (which may beneficially have a viscosity as measured by oscillatory rheology as described above that is at least ten-fold, beneficially at least one-hundred-fold, more beneficially at least five-hundred-fold, greater than a viscosity as measured by flow rheology as described above) with a second condensation-cure composition portion (which may beneficially have a viscosity as measured by oscillatory viscosity as described above that is at least ten-fold, beneficially at least one-hundred-fold, more beneficially at least five-hundred-fold, greater than a viscosity as measured by flow rheology as described above) to form a crosslinkable condensation-cure composition (e.g., one suitable for immediate delivery to a subject and preferably having one or more viscosity and/or cure characteristics such as those described above). In some of these embodiments, the crosslinkable condensation-cure compositions may be provided by combining (a) a first condensation-cure composition portion that comprises a first polysiloxane having two or more alkoxy groups, a first silanol compound having two or more silanol groups, and a first filler with (b) a second condensation-cure composition portion that comprises a catalyst for catalyzing a reaction between the alkoxy groups and the silanol groups, a second filler (which may be the same as or different from the first filler) and a diluent.

In certain embodiments, a physical crosslinking agent comprising a plurality of hydrogen bonding groups (e.g., —OH groups, —NH groups, etc.) may be provided within either one or both of the first and second condensation-cure composition portions that are combined to form of the crosslinkable condensation-cure compositions of the present disclosure. In embodiments where a first physical crosslinking agent is provided within the first condensation-cure composition portion and a second physical crosslinking agent is provided within the second condensation-cure composition portion, the first and second catalysts physical crosslinking agents may be the same or different.

In various embodiments, an imaging agent may be provided within either one or both of the first and second condensation-cure composition portions that are combined to form of the crosslinkable condensation-cure compositions of the present disclosure. In embodiments where a first imaging agent is provided within the first condensation-cure composition portion and a second imaging agent is provided within the second condensation-cure composition portion, the first and second imaging agents may be the same or different.

In some embodiments, the alkoxy groups of the polysiloxane having two or more alkoxy groups may be selected from C1-C5 alkoxy groups (methoxy, ethoxy, propoxy, butoxy, pentoxy, etc.). In some embodiments, the alkoxy groups of the polysiloxane having two or more alkoxy groups may be terminal alkoxy groups, pendant alkoxy groups (i.e., side groups), or a combination of both types of groups.

In some embodiments, the polysiloxane having two or more alkoxy groups contains pendant alkoxy groups and is a poly(dialkoxysiloxane), such as a poly(diethoxysiloxane) of the formula,

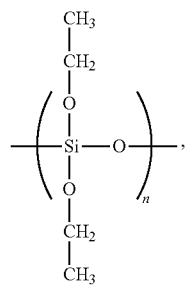

where n is an integer, for example, PSI-021 available from Gelest.

In various embodiments, the catalyst for catalyzing a reaction between the alkoxy groups and the silanol groups within the condensation-cure compositions of the present disclosure may be selected from a metal-based catalyst, such as a tin-, zinc- or titanium-based catalyst (e.g., Tin (II) ethylhexanoate or Titanium (IV) isopropoxide (Ti(OiPr)$_4$), or an acid or base catalyst.

In various embodiments, silanol compounds for use in conjunction with condensation-cure compositions of the present disclosure include silanol-terminated polymers, such as hydroxy-terminated polysiloxanes, for example,

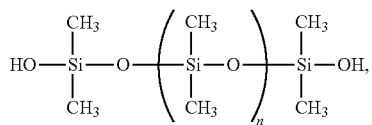

where n is an integer. Specific examples of such materials include DMS-S12, DMS-S21 and DMS-S31 available from Gelest, Inc. In certain embodiments, hydroxy-terminated polysiloxanes may be selected which have a weight average molecular weight that is between 500 and 30,000 Daltons.

In various embodiments, the diluent for use in conjunction with condensation-cure compositions of the present disclosure may be a relatively inert liquid, for example, a polysiloxane-based diluent, such as a trialkylsiloxy-terminated polysiloxane, for instance, a trimethylsiloxy-terminated PDMS. Other diluents include other non-polar solvents or oils.

In various embodiments, fillers for use in conjunction with the condensation-cure compositions of the present disclosure can be selected from various inorganic fillers, such as carbon fillers (e.g., carbon black), metal oxide fillers (e.g., titanium dioxide, zinc oxide, etc.), carbonate fillers (e.g., calcium carbonate), and silica fillers. Silica fillers, including fumed, precipitated, platelet and passivated silica fillers, are available in a range of sizes and surface areas and are available from a variety of vendors, including Sigma Aldrich. In certain embodiments, silica fillers may be characterized by a surface area of 100-500 m²/& among other possible values. Fillers for use in the present disclosure may range in aggregate particle size from 0.1 to 1.0 μm, among other values, for example, ranging from 0.01 to 10.0 μm in aggregate particle size, among other possibilities.

As noted above, the addition of the fillers will typically improve mechanical properties (e.g., tensile strength, compressive strength, elastic modulus and/or durometer) of the final cured material and, in certain embodiments, the fillers are selected to provide the condensation-cure compositions (i.e., the final condensation-cure compositions, as well as the first and second condensation-cure composition portions used to form the same) with shear-thinning or thixotropic fluid properties, for example, to ensure that the compositions have a viscosity as measured by oscillatory rheology at 0.1 Hz and 1% strain at 25° C. that is preferably by at least ten-fold, beneficially at least one-hundred-fold, more beneficially at least five-hundred-fold, greater than a viscosity as measured by flow rheology at a frequency of 30 Hz at 25° C.

In various embodiments, imaging agents for use in conjunction with the condensation-cure compositions of the present disclosure can be selected from those described above for use in conjunction with the addition-cure compositions and include MRI contrast agents, ultrasound contrast agents, and radiopaque agents, such as radiopaque metals, radiopaque metal alloys, radiopaque metal oxides and radiopaque polymers, including iodinated polymers. In particular embodiments, the radiopaque agent may be selected from tantalum, tungsten, bismuth (III) oxide, zinc oxide, titanium dioxide and zinc titanate.

In some embodiments, physical crosslinking agents may be used in conjunction with the condensation-cure compositions of the present disclosure, can be selected from those described above for use in conjunction with the addition-cure compositions, and may comprise a plurality of hydroxy (—OH) groups as hydrogen bonding groups. Examples of physical crosslinking agents include, hydroxy-terminated polymers and dendrimers such as hydroxy-terminated polysiloxanes (e.g., carbinol (hydroxy) terminated polydimethylsiloxane), hydroxy-terminated poly(alkylene oxides) including hydroxy-terminated polyethylene oxide and hydroxy-terminated polypropylene oxide, and hydroxy-terminated polyvinyl alcohol. Such hydroxy-terminated polymers may be, for example, linear, or may be multiarmed or dendritic, for example, having three, four, five, six or more arms, one specific example of which is a three-arm polymer of the formula,

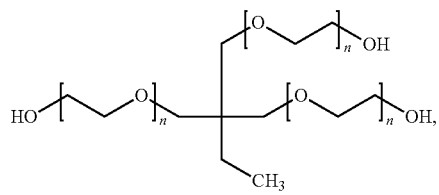

where n is an integer. Other examples include sugars, such as sucrose, cellulose, glucose, and dextrose, and potassium phthalate, polyols (e.g., glycerol, diglycerol, triglycerol, tetraglycerol, pentaglycerol, hexaglycerol, ethylene glycol, propylene glycol, butylene glycol, 1,5-pentane diol, 1,6-hexane diol, trimethylolpropane, 1,2,6-hexane triol, pentaerythritol, sorbitol, mannitol, hydroxypropylmethylcellulose or hydroxypropylethylcellulose) and acrylates (e.g. poly (acrylic acid), 2-hydroxyethylmethacrylate, poly (methyl methacrylate-co-ethyl acrylate)). Such physical crosslinkers may be provided, for example, in a concentration ranging from 0.5 to 5 wt %, typically 1.0 to 4.0 wt %, more typically about 1.25-3.5 wt %, among other possible amounts.

As above, in certain embodiments, the physical crosslinking agents may be selected to increase the resting viscosity (i.e., the zero-shear viscosity) of the condensation-cure compositions (i.e., the final condensation-cure compositions, as well as the first and second condensation-cure composition portions used to form the same), without significantly impacting the shear-thinning characteristics of the material. In this regard, as noted above, the addition of a silanol compound may act to decrease the resting viscosity of the condensation-cure compositions described herein. By providing physical crosslinking agents such as those described hereinabove, resting viscosity may be increased, without significantly impacting the shear-thinning characteristics of the material.

In various aspects, systems are provided in which compositions, including the addition-cure compositions and condensation-cure compositions described herein, are delivered from a delivery device to a site on or within a patient.

In some embodiments, the systems may comprise a first composition portion (e.g., a first addition-cure composition portion or a first condensation-cure composition portion) and a second composition portion (e.g., a second addition-cure composition portion or a second condensation-cure composition portion) as described hereinabove, which remain separated from each other within the delivery device until the time of delivery.

In some embodiments, the delivery device is configured to mix the first and second composition portions to form an addition-cure or condensation-cure composition in the delivery device and then deliver the addition-cure or condensation-cure composition to a site on or within a patient.

For example, the delivery device may comprise a first container comprising a first composition portion, a second container comprising a second composition portion, a mixer and a delivery catheter. The mixer may be, for example, a passive mixer or a dynamic mixer. In certain embodiments, the distal end of the catheter may be sized to fit within a femoral artery, a lumbar artery, or an inferior mesenteric artery, among other locations, including other vascular and non-vascular locations such as those listed above, among many others.

In certain embodiments, the catheter may have a proximal end and a distal end and may comprise a lumen having a proximal end and a distal end. The mixer may be (a) attached to or incorporated into the proximal end of the catheter or (b) configured to be in line with the proximal end of the catheter. In these embodiments, the mixer may, for example, comprise a first port configured for fluid communication with the first composition portion in the first container, a second port configured for fluid communication with the second composition portion in the second container, and a third port configured for fluid communication with the proximal end of the lumen of the catheter.

In certain embodiments, the catheter may comprise a first lumen having a proximal end and a distal end and a second lumen having a proximal end and a distal end, and the catheter may be configured to receive the first composition portion at the proximal end of the first lumen and to receive the second composition portion at the proximal end of the second lumen. Furthermore, the mixer may be (a) attached to or incorporated into the distal end of the catheter or (b) configured to be attached to the distal end of the catheter. In these embodiments, the mixer may, for example, comprise a first port configured for fluid communication with the distal end of the first lumen of the catheter, a second port configured for fluid communication with the distal end of the second lumen of the catheter, and a third port configured for fluid communication with a delivery site within a patient.

The first and second containers containing the first and second composition portions may be, for example, syringes or compliant chambers. In certain embodiments, the delivery system may further include a multiple-barreled syringe apparatus having at least first and second barrels joined together (e.g., by a flange) and containing the respective the first and second composition portions. Parallel plungers joined together (e.g., by a second flange) can be used to force the first and second composition portions from the first and second barrels to discharge the first and second composition portions at the same rate (or in the case where the first and barrels are of different diameter at a fixed ratio). An example of a barrel of this type is described in US Pat. Pub. No. 20070129672A1 for use in epoxy systems.

As noted above, in certain embodiments, addition-cure and condensation-cure compositions in accordance with the present disclosure may be delivered into a body of a patient. For example, compositions in accordance with the present disclosure may be dispensed onto any tissue or into any body cavity or body lumen of a patient, including, for example, a fallopian tube, a ureter, or the vasculature of a patient, including an abdominal aortic aneurysm, among various other locations. For example, the compositions may be used in a number of applications including vascular embolization, treatment of arteriovenous malformation, treatment of AV fistulas, treatment of abdominal aortic aneurysms, intracranial aneurysms or pulmonary aneurysm, space filling and bulking in a variety of tissues, prevention of tissue adhesion, hernia repair, treatment of reflux, temporary or permanent occlusion of body lumens for a variety of applications including sterilization and prevention of calculus migration during lithotripsy, and treatment of hemorrhage.

In certain embodiments, the system may comprise an endoprosthesis. For example, the endoprosthesis may be a stent graft. The endoprosthesis may be configured to span an abdominal aortic aneurysm in some embodiments. In certain of these embodiments, the endoprosthesis configured to span the aneurysm may be delivered into the aneurysm, and the composition may be delivered between an outer surface of the endoprosthesis and an inner wall of the aneurysm.

Example 1. PDMS Alkoxy-Silanol Formulation with Silica Filler

Formulations were comprised of two phases (A and B as shown in Table 1) to keep the formulation catalyst separate from the reactive (silanol and alkoxy) groups.

TABLE 1

| 4:1 Mixing Ratio | Description | Material Part # | Manufacturer | Mass % |
|---|---|---|---|---|
| Phase A | Filler | Fumed Silica | Sigma Aldrich | 4.50% |
| | Silanol | DMS-S21 | Gelest | 28.65% |
| | Silanol | DMS-S31 | Gelest | 50.93% |
| | Crosslinker | PSI-021 | Gelest | 15.92% |
| Phase B | Filler | Fumed Silica | Sigma Aldrich | 4.50% |
| | Diluent | DMS-T21 | Gelest | 85.52% |
| | Radiopaque Agent | Bismuth (III) Oxide | Alfa Aesar | 7.51% |
| | Catalyst | Tin (II) ethylhexanoate | Sigma Aldrich | 2.46% |

Each phase was mixed in an appropriate size speed mix cup using a planetary mixer (speed mixer) for 60 seconds at 2000 rpm. Information on the speed mixing implements for formulating individual phases can be found below in Table 2.

TABLE 2

| Component | Manufacturer | Part Number |
|---|---|---|
| Speed mixing cups | FlackTek (Landrum, SC, USA) | Various Sizes |
| Planetary mixer | FlackTek | DAC 600 |

Example 2. PDMS Vinyl-Hydride with Silica Filler

Formulations were comprised of two phases (A and B as shown in Table 3) to separate the platinum catalyst from the hydride-functionalized PDMS. Each phase was mixed in an appropriate size speed mix cup using a planetary mixer.

TABLE 3

| Mixed 2:1 (A:B) by volume | Description | Material Part # | Manufacturer | Mass % |
|---|---|---|---|---|
| Phase A | Filler | Fumed Silica | Sigma Aldrich | 4.00% |
| | Vinyl Terminated PDMS | DMS-V22 | Gelest | 80.00% |
| | Vinyl Crosslinker | VDT-131 | Gelest | 12.45% |
| | Radiopaque Agent | Bismuth (III) Oxide | Alfa Aesar | 2.50% |
| | Platinum Catalyst | SIP6830.3 | Gelest | 0.93% |
| | Vinyl Catalyst Modifier | SIT7900.0 | Gelest | 0.12% |
| Phase B | Filler | Fumed Silica | Sigma Aldrich | 4.00% |
| | Hydride Crosslinker | HMS-151 | Gelest | 16.00% |
| | Hydride Terminated PDMS | DMS-H25 | Gelest | 80.00% |

Example 3. PDMS Vinyl-Hydride with Silica Filler

Formulations were comprised of two phases (A and B as shown in Tables 4 to 11) to separate the platinum catalyst from the hydride-functionalized PDMS. Each phase was mixed in an appropriate size speed mix cup using a planetary mixer.

TABLE 4

Formula VHS65A (mixed 1:1 by volume)

| Component | Product | Supplier | wt % |
|---|---|---|---|
| Phase A | | | |
| Vinyl PDMS | GP-977 | Genesee Polymers | 74.25% |
| Platinum Catalyst | SIP6830.3 | Gelest | 1.05% |
| Catalyst Modifier | SIT7900.0 | Gelest | 0.20% |
| Fumed Silica Filler | S5505 | Sigma Aldrich | 9.00% |
| Physical Crosslinker | 416177 | Sigma Aldrich | 1.50% |
| Bismuth Oxide | 46314 | Alfa Aesar | 5.00% |
| Silanol PDMS | DMS-S12 | Gelest | 9.00% |
| Phase B | | | |
| Hydride Crosslinker | CP-6900 | Genesee Polymers | 10.00% |
| High MW Hydride PDMS | GP-536 | Genesee Polymers | 13.88% |
| Low MW Hydride PDMS | GP-499 | Genesee Polymers | 29.62% |
| Vinyl PDMS | GP-977 | Genesee Polymers | 22.00% |
| Fumed Silica Filler | S5505 | Sigma Aldrich | 9.00% |
| Physical Crosslinker | 416177 | Sigma Aldrich | 1.50% |
| Bismuth Oxide | 46314 | Alfa Aesar | 5.00% |
| Silanol PDMS | DMS-S12 | Gelest | 9.00% |

TABLE 5

Formulation VHS68 (mixed 1:1 by volume)

| Component | Product | Supplier | Mass % |
|---|---|---|---|
| Phase A | | | |
| Vinyl PDMS | GP-977 | Genesee | 75.75% |
| Physical Crosslinker | Sucrose 1800 g/L (aqueous) | N/A | 2.00% |
| Silanol PDMS | DMS-S12 | Gelest | 8.00% |
| Platinum Catalyst | SIP6830.3 | Gelest | 1.05% |
| Fumed Silica Filler | Fumed Silica | Sigma | 8.00% |
| Catalyst Modifier | SIT7900.0 | Gelest, 8K-34454 | 0.20% |
| Bismuth Oxide | Bismuth Oxide | Alfa, U23D045 | 5.00% |
| Phase B | | | |
| High MW Hydride PDMS | GP-536 | Genesee | 16.57% |
| Low MW Hydride PDMS | GP-499 | Genesee | 29.23% |
| Vinyl PDMS | GP-977 | Genesee | 21.20% |
| Physical Crosslinker | TMPEO-1000 | Sigma | 3.00% |
| Silanol PDMS | DMS-S12 | Gelest | 7.50% |
| Hydride Crosslinker | CP-6900 | Genesee | 10.00% |
| Bismuth Oxide | Bismuth Oxide | Alfa, U23D045 | 5.00% |
| Fumed Silica Filler | S5505 | Sigma Aldrich | 7.50% |

TABLE 6

Formulation VHS68A (mixed 1:1 by volume)

| Component | Product | Supplier | Mass % |
|---|---|---|---|
| Phase A | | | |
| Vinyl PDMS | GP-977 | Genesee | 74.75% |
| Physical Crosslinker | Sucrose 1800 g/L (aqueous) | N/A | 2.00% |
| Silanol PDMS | DMS-S12 | Gelest | 8.50% |
| Platinum Catalyst | SIP6830.3 | Gelest | 1.05% |
| Fumed Silica Filler | Fumed Silica | Sigma | 8.50% |
| Catalyst Modifier | SIT7900.0 | Gelest, 8K-34454 | 0.20% |
| Bismuth Oxide | Bismuth Oxide | Alfa, U23D045 | 5.00% |
| Phase B | | | |
| High MW Hydride PDMS | GP-536 | Genesee | 16.10% |
| Low MW Hydride PDMS | GP-499 | Genesee | 28.40% |
| Vinyl PDMS | GP-977 | Genesee | 21.50% |
| Physical Crosslinker | TMPEO-1000 | Sigma | 3.00% |
| Silanol PDMS | DMS-S12 | Gelest | 8.00% |
| Hydride Crosslinker | CP-6900 | Genesee | 10.00% |
| Bismuth Oxide | Bismuth Oxide | Alfa, U23D045 | 5.00% |
| Fumed Silica Filler | Fumed Silica | Sigma | 8.00% |

TABLE 7

Formulation VHS68B (mixed 1:1 by volume)

| Component | Product | Supplier | Mass % |
|---|---|---|---|
| Phase A | | | |
| Vinyl PDMS | GP-977 | Genesee | 71.75% |
| Physical Crosslinker | Sucrose 1800 g/L (aqueous) | N/A | 2.00% |
| Silanol PDMS | DMS-S12 | Gelest | 10.00% |
| Platinum Catalyst | SIP6830.3 | Gelest | 1.05% |
| Fumed Silica Filler | Fumed Silica | Sigma | 10.00% |
| Catalyst Modifier | SIT7900.0 | Gelest, 8K-34454 | 0.20% |
| Bismuth Oxide | Bismuth Oxide | Alfa, U23D045 | 5.00% |
| Phase B | | | |
| High MW Hydride PDMS | GP-536 | Genesee | 15.19% |
| Low MW Hydride PDMS | GP-499 | Genesee | 26.81% |
| Vinyl PDMS | GP-977 | Genesee | 21.00% |
| Physical Crosslinker | TMPEO-1000 | Sigma | 3.00% |
| Silanol PDMS | DMS-S12 | Gelest | 9.50% |
| Hydride Crosslinker | CP-6900 | Genesee | 10.00% |
| Bismuth Oxide | Bismuth Oxide | Alfa, U23D045 | 5.00% |
| Fumed Silica Filler | Fumed Silica | Sigma | 9.50% |

TABLE 8

Formulation VHS68C (mixed 1:1 by volume)

| Component | Product | Supplier | Mass % |
|---|---|---|---|
| Phase A | | | |
| Vinyl PDMS | GP-977 | Genesee | 75.25% |
| Physical Crosslinker | Sucrose 1800 g/L (aqueous) | N/A | 2.00% |
| Silanol PDMS | DMS-S12 | Gelest | 8.25% |
| Platinum Catalyst | SIP6830.3 | Gelest | 1.05% |
| Fumed Silica Filler | Fumed Silica | Sigma | 8.25% |
| Catalyst Modifier | SIT7900.0 | Gelest, 8K-34454 | 0.20% |
| Bismuth Oxide | Bismuth Oxide | Alfa, U23D045 | 5.00% |
| Phase B | | | |
| High MW Hydride PDMS | GP-536 | Genesee | 16.39% |
| Low MW Hydride PDMS | GP-499 | Genesee | 28.91% |
| Vinyl PDMS | GP-977 | Genesee | 21.20% |
| Physical Crosslinker | TMPEO-1000 | Sigma | 3.00% |
| Silanol PDMS | DMS-S12 | Gelest | 7.75% |
| Hydride Crosslinker | CP-6900 | Genesee | 10.00% |
| Bismuth Oxide | Bismuth Oxide | Alfa, U23D045 | 5.00% |
| Fumed Silica Filler | Fumed Silica | Sigma | 7.75% |

TABLE 9

Formulation VHS68D (mixed 1:1 by volume)

| Component | Product | Supplier | Mass % |
|---|---|---|---|
| Phase A | | | |
| Vinyl PDMS | GP-977 | Genesee | 70.75% |
| Physical Crosslinker | Sucrose 1800 g/L (aqueous) | N/A | 2.00% |
| Silanol PDMS | DMS-S12 | Gelest | 10.50% |
| Platinum Catalyst | SIP6830.3 | Gelest | 1.05% |
| Fumed Silica Filler | Fumed Silica | Sigma | 10.50% |
| Catalyst Modifier | SIT7900.0 | Gelest, 8K-34454 | 0.20% |
| Bismuth Oxide | Bismuth Oxide | Alfa, U23D045 | 5.00% |
| Phase B | | | |
| High MW Hydride PDMS | GP-536 | Genesee | 15.19% |
| Low MW Hydride PDMS | GP-499 | Genesee | 26.81% |
| Vinyl PDMS | GP-977 | Genesee | 20.00% |
| Physical Crosslinker | TMPEO-1000 | Sigma | 3.00% |
| Silanol PDMS | DMS-S12 | Gelest | 10.00% |
| Hydride Crosslinker | CP-6900 | Genesee | 10.00% |
| Bismuth Oxide | Bismuth Oxide | Alfa, U23D045 | 5.00% |
| Fumed Silica Filler | Fumed Silica | Sigma | 10.00% |

TABLE 10

Formulation VHS68E (mixed 1:1 by volume)

| Component | Product | Supplier | Mass % |
|---|---|---|---|
| Phase A | | | |
| Vinyl PDMS | GP-977 | Genesee | 74.25% |
| Physical Crosslinker | Sucrose 1800 g/L (aqueous) | N/A | 2.00% |
| Silanol PDMS | DMS-S12 | Gelest | 8.75% |
| Platinum Catalyst | SIP6830.3 | Gelest | 1.05% |
| Fumed Silica Filler | Fumed Silica | Sigma | 8.75% |
| Catalyst Modifier | SIT7900.0 | Gelest, 8K-34454 | 0.20% |
| Bismuth Oxide | Bismuth Oxide | Alfa, U23D045 | 5.00% |
| Phase B | | | |
| High MW Hydride PDMS | GP-536 | Genesee | 16.02% |
| Low MW Hydride PDMS | GP-499 | Genesee | 28.28% |
| Vinyl PDMS | GP-977 | Genesee | 21.20% |
| Physical Crosslinker | TMPEO-1000 | Sigma | 3.00% |
| Silanol PDMS | DMS-S12 | Gelest | 8.25% |
| Hydride Crosslinker | CP-6900 | Genesee | 10.00% |
| Bismuth Oxide | Bismuth Oxide | Alfa, U23D045 | 5.00% |
| Fumed Silica Filler | Fumed Silica | Sigma | 8.25% |

TABLE 11

Formulation VHS68F (mixed 1:1 by volume)

| Component | Product | Supplier | Mass % |
|---|---|---|---|
| Phase A | | | |
| Vinyl PDMS | GP-977 | Genesee | 71.25% |
| Physical Crosslinker | Sucrose 1800 g/L (aqueous) | N/A | 2.00% |
| Silanol PDMS | DMS-S12 | Gelest | 10.25% |
| Platinum Catalyst | SIP6830.3 | Gelest | 1.05% |
| Fumed Silica Filler | Fumed Silica | Sigma | 10.25% |
| Catalyst Modifier | SIT7900.0 | Gelest, 8K-34454 | 0.20% |
| Bismuth Oxide | Bismuth Oxide | Alfa, U23D045 | 5.00% |
| Phase B | | | |
| High MW Hydride PDMS | GP-536 | Genesee | 15.28% |
| Low MW Hydride PDMS | GP-499 | Genesee | 26.97% |
| Vinyl PDMS | GP-977 | Genesee | 20.25% |
| Physical Crosslinker | TMPEO-1000 | Sigma | 3.00% |
| Silanol PDMS | DMS-S12 | Gelest | 9.75% |
| Hydride Crosslinker | CP-6900 | Genesee | 10.00% |
| Bismuth Oxide | Bismuth Oxide | Alfa, U23D045 | 5.00% |
| Fumed Silica Filler | Fumed Silica | Sigma | 9.75% |

For the Phase A and Phase B of each of the formulations of Tables 4-11, viscosity measured by flow rheology at a frequency of 30 Hz at 25° C. ("Flow Viscosity") and oscillatory rheology at 1% strain and 0.1 Hz at 25° C. ("Phase Viscosity (Osc.)"). Also shown is the dispense viscosity which is measured by oscillatory rheology at 1% strain and 0.1 Hz at 25° C. Further shown is the gel time, which is based on measurements taken at constant frequency and strain (f=10 rad/s, γ=1%) over the course of 90 minutes to observe the cure time and profile, wherein gel time is defined as the time at which a peak of the phase angle (δ) is observed.

TABLE 12

| Formulation | Phase A Viscosities (Pa*s) | | Phase B Viscosities (Pa*s) | | Dispense Viscosity (Pa*s) | Gel Time (Min.) |
|---|---|---|---|---|---|---|
| | Phase Viscosity (Osc.) | Flow Viscosity | Phase Viscosity (Osc.) | Flow Viscosity | | |
| VHS65A | 21055 | 21 | 11794 | 12 | 13418 | 21 |
| VHS68  | 16693 | 19 | 15926 | 20 |  9053 | 22 |
| VHS68A | 19134 | 23 | 20074 | 23 | 11369 | 21 |
| VHS68B | 17567 | 18 | 18129 | 20 | 10851 | 20 |
| VHS68C | 15577 | 18 | 14777 | 21 |  8329 | 23 |
| VHS68D | 19195 | 19 | 21109 | 19 | 15166 | 23 |
| VHS68E | 18487 | 19 | 16120 | 22 | 12440 | 21 |
| VHS68F | 21583 | 20 | 25824 | 24 | 14682 | 22 |

The invention claimed is:

1. A method for in situ forming a crosslinked composition at a delivery site in the body of a patient, the method comprising:
    delivering a first addition-cure composition to the delivery site, the first addition-cure composition including a polydimethylsiloxane polymer, a catalyst, and a first fumed silica;
    delivering a second addition-cure composition to the delivery site, the second addition-cure composition including a first hydride polydimethylsiloxane polymer having a first molecular weight of 4 to 10 kDa, a second hydride polydimethylsiloxane polymer having a second molecular weight of 11 to 20 kDa, a second fumed silica, and a crosslinker, the first and/or second addition-cure composition includes a tantalum radiopaque agent; and
    combining at the delivery site the first and second addition-cure compositions to form a crosslinkable composition that is cured to form the crosslinked composition at the delivery site.

2. The method of claim 1, wherein the first and second addition-cure compositions include a tantalum radiopaque agent.

3. The method of claim 1, wherein the catalyst is a platinum catalyst.

4. The method of claim 1, wherein the first and second fumed silicas are the same.

5. The method of claim 1, wherein the polydimethylsiloxane polymer is a vinyl-terminated polydimethylsiloxane.

6. The method of claim 1, wherein the first hydride polydimethylsiloxane polymer has two or more hydride groups.

7. A method for in situ forming a crosslinked composition at a delivery site in the body of a patient, the method comprising:
    delivering a first addition-cure composition to the delivery site via a multi-barrel syringe, the first addition-cure composition including a polydimethylsiloxane polymer, a catalyst, and a first fumed silica;
    delivering a second addition-cure composition to the delivery site via the multi-barrel syringe, the second addition-cure composition including a first hydride polydimethylsiloxane polymer having a first molecular weight of 4 to 10 kDa, a second hydride polydimethylsiloxane polymer having a second molecular weight of 11 to 20 kDa, a second fumed silica, and a crosslinker, the first and/or second addition-cure composition includes a tantalum radiopaque agent; and
    combining at the delivery site the first and second addition-cure compositions to form a crosslinkable composition that is cured to form the crosslinked composition at the delivery site.

8. The method of claim 7, wherein the first and second addition-cure compositions include a tantalum radiopaque agent.

9. The method of claim 7, wherein the catalyst is a platinum catalyst.

10. The method of claim 7, wherein the first and second fumed silicas are the same.

11. The method of claim 7, wherein the polydimethylsiloxane polymer is a vinyl-terminated polydimethylsiloxane.

12. The method of claim 7, wherein the first hydride polydimethylsiloxane polymer has two or more hydride groups.

13. A formulation for in situ forming a crosslinked composition at a delivery site in the body of a patient, the formulation comprising:
    a first addition-cure composition including a polydimethylsiloxane polymer, a catalyst, and a first fumed silica;
    a second addition-cure composition including a first hydride polydimethylsiloxane polymer having a first molecular weight of 4 to 10 kDa, a second hydride polydimethylsiloxane polymer having a second molecular weight of 11 to 20 kDa, a second fumed silica, and a crosslinker, the first and/or second addition-cure composition includes a tantalum radiopaque agent,
    when combined, the first and second addition-cure compositions configured to form a crosslinkable composition curable to form the crosslinked composition at the delivery site.

14. The method of claim 13, wherein the first and second addition-cure compositions include a tantalum radiopaque agent.

15. The method of claim 13, wherein the catalyst is a platinum catalyst.

16. The method of claim 13, wherein the first and second fumed silicas are the same.

17. The method of claim 13, wherein the polydimethylsiloxane polymer is a vinyl-terminated polydimethylsiloxane.

* * * * *